US007361206B1

(12) United States Patent
Jahn et al.

(10) Patent No.: US 7,361,206 B1
(45) Date of Patent: Apr. 22, 2008

(54) APPARATUS AND METHOD FOR WATER VAPOR REMOVAL IN AN ION MOBILITY SPECTROMETER

(75) Inventors: Michael D. Jahn, Jasper, IN (US); Matthew Todd Griffin, Bloomington, IN (US); Norman Popkie, Jr., Oolitic, IN (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 456 days.

(21) Appl. No.: 10/943,645

(22) Filed: Sep. 7, 2004

(51) Int. Cl.
*B01D 53/22* (2006.01)
*B01D 53/04* (2006.01)
*G01N 30/14* (2006.01)

(52) U.S. Cl. .................. 95/52; 95/82; 95/117; 95/139; 96/4; 96/8; 96/9; 96/101; 96/105; 96/108; 73/23.37; 73/23.41; 73/23.42

(58) Field of Classification Search .................. 95/43, 95/45, 51, 52, 82, 90, 117, 139, 901, 903; 96/4, 8, 10, 101, 105, 108, 9; 73/23.2, 23.35, 73/23.37, 23.41, 23.42
See application file for complete search history.

(56) References Cited

U.S. PATENT DOCUMENTS

| | | | | |
|---|---|---|---|---|
| 3,398,505 A | * | 8/1968 | Llewellyn | 96/102 |
| 3,735,558 A | * | 5/1973 | Skarstrom et al. | 95/52 |
| 4,293,316 A | * | 10/1981 | Block | 96/4 |
| 4,322,669 A | | 3/1982 | Fukuma et al. | 318/571 |
| 4,390,784 A | | 6/1983 | Browning et al. | 250/287 |
| 4,451,624 A | | 5/1984 | Howes | 526/292.2 |
| 4,466,202 A | * | 8/1984 | Merten | 95/52 |
| 4,793,830 A | * | 12/1988 | Murphy et al. | 95/52 |
| 4,952,219 A | * | 8/1990 | DiMartino, Sr. | 95/52 |
| 5,035,726 A | * | 7/1991 | Chen et al. | 95/54 |
| 5,162,652 A | | 11/1992 | Cohen et al. | 250/288 |
| 5,259,869 A | * | 11/1993 | Auvil et al. | 95/52 |
| 5,283,199 A | | 2/1994 | Bacon, Jr. et al. | 436/173 |
| 5,344,480 A | * | 9/1994 | Schulte et al. | 95/52 |
| 5,405,781 A | | 4/1995 | Davies et al. | 436/52 |
| 5,457,316 A | | 10/1995 | Cohen et al. | 250/286 |
| 5,491,337 A | | 2/1996 | Jenkins et al. | 250/287 |
| 6,291,821 B1 | | 9/2001 | Danylewych-May et al. | 250/286 |
| 6,440,196 B1 | * | 8/2002 | Chiappini et al. | 95/52 |

(Continued)

FOREIGN PATENT DOCUMENTS

EP 0 135 747 A2 * 4/1985

(Continued)

*Primary Examiner*—Jason M. Greene
(74) *Attorney, Agent, or Firm*—Christopher A. Monsey

(57) ABSTRACT

The present invention is directed to an apparatus and a method for continuously removing water vapor from a closed loop, re-circulated gas flow in an ion mobility spectrometer using a water permeable membrane, having a first side and a second side opposite the first side. The gas flow is disposed adjacent and carried past the first side to deposit water vapor that passes through the membrane to the second side. An exhaust flow is disposed adjacent and carried passed the second side of the membrane to remove the water vapor from the system. Therefore, the water removal apparatus continuously regenerates in-situ. Heaters, heat sinks and additional treatment systems including charcoal filters can also be included in the system to enhance its performance.

10 Claims, 4 Drawing Sheets

U.S. PATENT DOCUMENTS

| | | | |
|---|---|---|---|
| 6,642,513 B1 | 11/2003 | Jenkins et al. | 250/288 |
| 6,652,625 B1 * | 11/2003 | Tipler et al. | 95/82 |
| 6,656,738 B1 * | 12/2003 | Vogel et al. | 96/101 |
| 6,911,064 B2 * | 6/2005 | Fujii et al. | 95/52 |
| 2003/0201389 A1 | 10/2003 | Hartley | 250/287 |

FOREIGN PATENT DOCUMENTS

| | | | |
|---|---|---|---|
| EP | 0 920 619 | * | 2/1998 |
| WO | WO 96/28728 | * | 9/1996 |
| WO | WO 00/79261 A1 | * | 12/2000 |

* cited by examiner

APPARATUS AND METHOD FOR WATER VAPOR REMOVAL IN AN ION MOBILITY SPECTROMETER

GOVERNMENT LICENSING CLAUSE

The invention described herein may be manufactured and used by or for the Government of the United States of America for governmental purposes without the payment of any royalties thereon or therefore.

FIELD OF THE INVENTION

This invention relates to ion mobility spectrometry.

BACKGROUND OF THE INVENTION

Ion mobility spectrometry is used in chemical and biological agent detectors and provides good sensitivity, low power requirements, and operation at atmospheric conditions. In general, ion mobility spectrometry is a gas-phase ion separation technique that separates different chemical species as a function of both size, i.e. average collisional cross section area, and mass-to-charge ratio (m/z). The mass-to-charge ratio is the molecular weight of a species divided by the number of charges, which in many instances is one because that species is singly charged. In a typical ion mobility spectrometry device, a sample to be analyzed is collected and passed through an inlet and into an ion source region where ions are formed. The ions then pass along a drift tube containing a potential gradient that is used to accelerate the ions against a counter-current drift gas, e.g. air. Air is also used as a carrier gas to urge the ions into the drift tube. Under the influence of the accelerating voltage, the lighter and smaller ions, i.e. the ions having a smaller mass-to-charge ratio and average collisional cross section area, reach the detector first, and heavier and larger ions arrive later.

As the ions exit the drift tube, they collide with a detector or collector, for example a Faraday Cup. Since the ions exit the drift tube at different times, chemical species in the sample are identified based on known arrival times of certain ions at the detector. When a given ion or group of ions reach the detector, they create a voltage peak that is proportional to the number of ions striking the detector. These peaks are referred to as the ion mobility spectrometry spectra. The ion mobility spectrometry spectra are averaged to increase the signal-to-noise ratio (SNR) for a given measurement. Therefore, a time window for monitoring the detector is established and monitored for these peaks. In addition, a voltage threshold is established for each peak, and the number of peaks in excess of the voltage threshold is monitored. An alarm condition in the monitoring device is established for a given contaminant in the sample when a sufficient number of peaks above the voltage threshold that are associated with that contaminant are detected.

Ion mobility spectrometry begins by forming reactant ions through the interaction of reactant molecules with a radioactive source. Typically, sample ions are formed in the ionization region by collisions between reactant ions and sample molecules. This occurs in the gas phase by electron- or proton-transfer from reactant ions available in the ionization chamber to sample molecules, i.e. atmospheric pressure chemical ionization (APCI). A sweep gas is often used to urge the sample ions toward the drift tube. In addition, once the sample ions are admitted into the drift tube, they are exposed to both a potential gradient and a counter current drift gas. Since the analysis takes place at atmospheric conditions, air is often used as both the sweep gas and counter current drift gas which can contain varying amounts of water vapor.

Formation of ion clusters is a common problem in ion mobility spectrometry. The existence of water vapor in the sample flow increases the problem of ion clusters. Therefore, the sweep gas and counter current gas need to be as dry as possible. In the laboratory, drying of these gases can be facilitated by any process desired regardless of size, cost or complexity. When these analyzers are used in the field, however, size and cost are considerable concerns.

In field analyzers, the sample air is typically re-circulated in a closed-loop type system. Molecular sieves and charcoal filters are included in these closed-loop systems to remove the water vapor and organic compounds from the sample air. The molecular sieve and charcoal need to be changed, cleaned, replaced or re-activated regularly. In one system, for example, the molecular sieve and charcoal were provided as a removable cartridge that has to be replaced every 3-10 days depending on use, creating a need to monitor the system to determine when the cartridge needs to be replaced and adding an additional cost associated with the consumable cartridges.

Therefore, a system is needed for removing moisture or water vapor from the sample gases in an ion mobility spectrometry analyzer that can operate continuously and that eliminates the need for consumables.

SUMMARY OF THE INVENTION

The present invention is directed to an apparatus for removing water vapor from a gas flow in an ion mobility spectrometer. The apparatus includes a self-regenerating water vapor removal system capable of continuously removing water vapor from a closed-loop, re-circulated sample and counter current gas flow, for example ambient air, and regenerating itself in-situ. The water vapor removal apparatus includes a water permeable membrane, having a first side and a second side opposite the first side. The gas flow is disposed adjacent the first side, and an exhaust flow, for example ambient intake air, is disposed adjacent the second side of the membrane to remove water vapor that diffuses through the membrane. Heaters, heat sinks and additional treatment systems including charcoal filters can also be included in the apparatus of the present invention to enhance its performance.

The present invention is also directed to a method for using this apparatus to reduce the amount of water vapor in the closed-loop, re-circulated sample and counter current gas flow in the ion mobility spectrometer. In accordance with this method, the gas flow is passed through the in-situ, self-regenerating water vapor removal apparatus such that the gas flow passes adjacent a first side of the water permeable membrane and the water vapor passes through the membrane to the second side. The exhaust flow is concurrently passed adjacent the second side of the membrane to remove the water vapor and then is exhausted from the apparatus and the ion mobility spectrometer. The gas flow can be cooled, and the exhaust flow can be heated to enhance system performance. In addition, the gas flow can be passed through additional treatment systems, for example a charcoal filter, to achieve additional contaminant removal.

DETAILED DESCRIPTION

Figure 1:
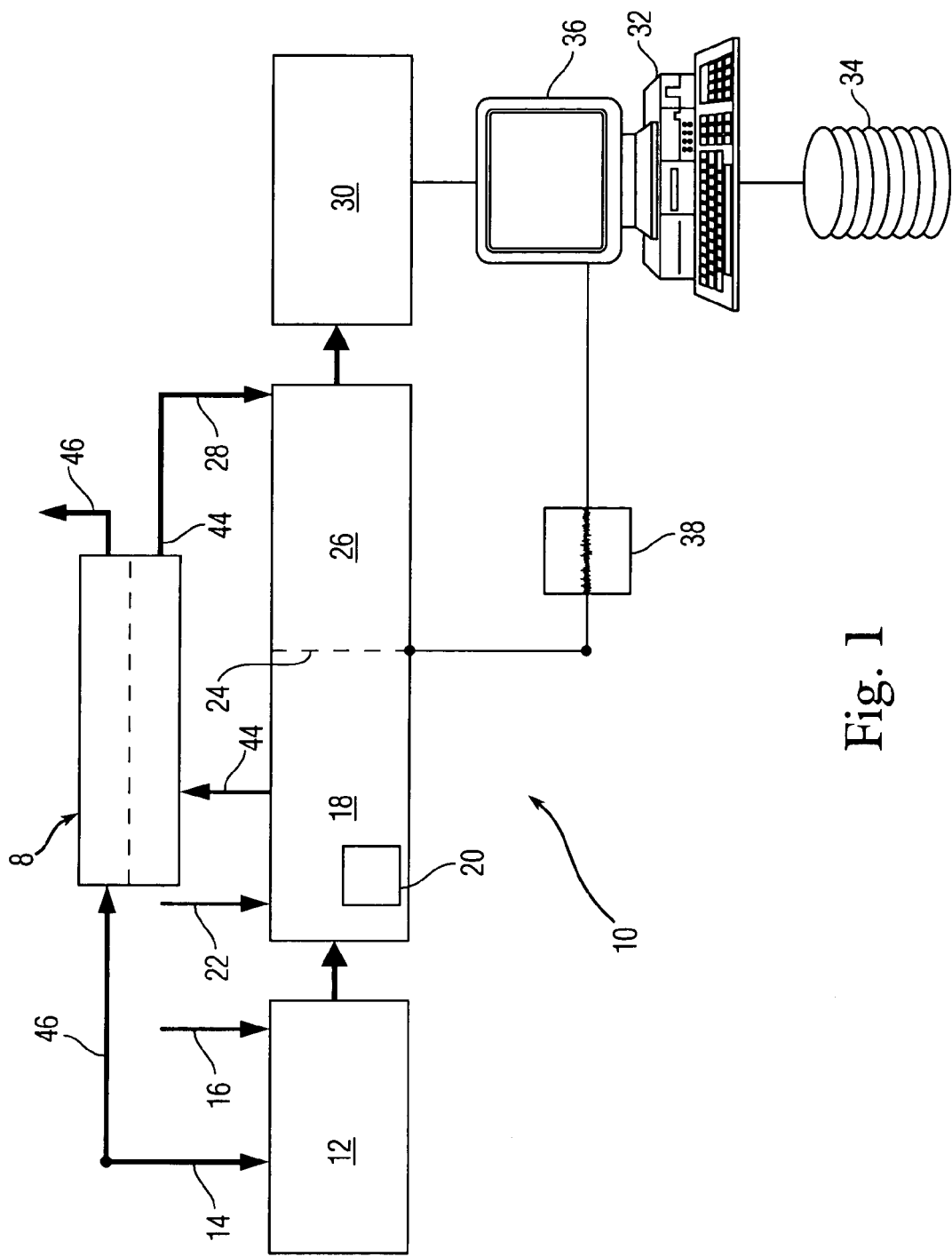
FIG. 1 is a schematic representation of an embodiment of the water vapor removal apparatus and ion mobility spectrometry system in accordance with the present invention.

Referring initially to FIG. 1, an apparatus 8 for removing water vapor from a gas flow in an ion mobility spectrometer (IMS) 10 in accordance with the present invention is illustrated. The IMS 10 can be an automated or manual system and can be stationary or portable and preferably operates at atmospheric pressure. In general, an IMS 10 includes an inlet region or assembly 12 having at least one sample inlet or intake 14 arranged to accept one or more samples to be analyzed. Suitable inlet region 12 arrangements are known and available in the art. The samples can be introduced into the inlet in a gaseous state or can be introduced in a liquid state and vaporized. The inlet assembly 12 can also include one or more reactant inlets 16 to provide for the introduction of reactant into the IMS system 10. Suitable reactants include acetone, ammonia and water, although others exist. In one embodiment, the reactants are introduced as a continuous liquid flow that is vaporized in the inlet region 12 and mixed with the gaseous or vaporized sample.

The IMS system 10 also includes an ionization region 18 in communication with the inlet region 12 and arranged to accept the gaseous mixture of sample and reactant and to ionize the gaseous sample to create sample or product ions for analysis. Suitable arrangements for the ionization region 18 are available and known in the art. The sample can pass directly into the ionization region 18 or can pass through a suitable filter or membrane 19 (FIG. 3) arranged to prevent particles, liquid or moisture from passing into the ionization region 18. The inlet membrane 19 can also act as a flow limiter and can select for the entry of either positive or negative ions. Suitable inlet membranes 19 are known and available in the art. The ionization region 18 includes an ionization source 20, for example a photoionization source, an electrospray ionization source, a corona discharge source, an alkali-bead emissive source or a radioactive source. In one embodiment, the ionization source 20 is a radioactive nickel ($^{63}$Ni) source. The ionization region 18 can also include a carrier or sweep gas flow 22 to sweep the ions that pass through the membrane 19 away from the membrane 19 and to urge those sample ions through the ionization region 18. Suitable sweep gases include air and inert gases, for example helium and nitrogen, among others.

The IMS system 10 further includes an ion gate, shutter gate, or gating grid 24. In one embodiment, the ion gate 24 is disposed at a first end of a drift tube 26. Alternatively, the ion gate 24 can be arranged as a divider that separates an ionization region from a drift region in a single drift tube structure. Suitable ion gates include Bradbury-Nielson ion gates. In general, the ion gate is arranged as a plurality of parallel and perpendicular wires or as a wire mesh to which a voltage is applied. By applying voltage to the ion gate 24, the ion gate 24 is capable of selectively, in for example an alternating fashion, being opened to admit sample ions into the drift tube 26 and being closed to repel sample ions from the drift tube 26. When the ion gate 24 is open, the ions of the correct polarity enter the drift region.

The drift tube 26 is typically an elongated or cylindrical assembly that includes an arrangement of conductive electrodes and insulators. Each electrode is charged to an appropriate electric potential to establish a uniform electric field extending through the drift tube 26. The drift tube also includes a countercurrent drift gas inlet 28 to provide for introduction of a drift gas counter-current flow 29 (FIG. 3) into the drift tube 26 flowing opposite to the direction that the sample ions travel under the force of the electric field. Suitable drift gases include air and inert gases, for example helium and nitrogen, among others.

The sample ions, upon entering the drift tube 26, are separated as they are accelerated through the drift tube by the electric field against the counter current neutral drift gas. The time it takes for the sample ions to travel the length of the drift tube 26 is variable and depends upon mass, geometry, size and charge, producing a distinct transit time through the drift tube 26 that is characteristic of the sample being tested.

The IMS system 10 also includes an ion detector 30 disposed adjacent a second end of the drift tube 26 opposite the first end. The ion detector 30 is arranged such that the sample ions exiting the drift tube 26 collide with the ion detector, generating a current that is proportional to the number of sample ions colliding with the detector at any given time. Since the sample ions exit the drift tube over a given time period, the ion detector 30 is capable of generating a time dependent voltage output, called a mobility spectrum.

Figure 2:
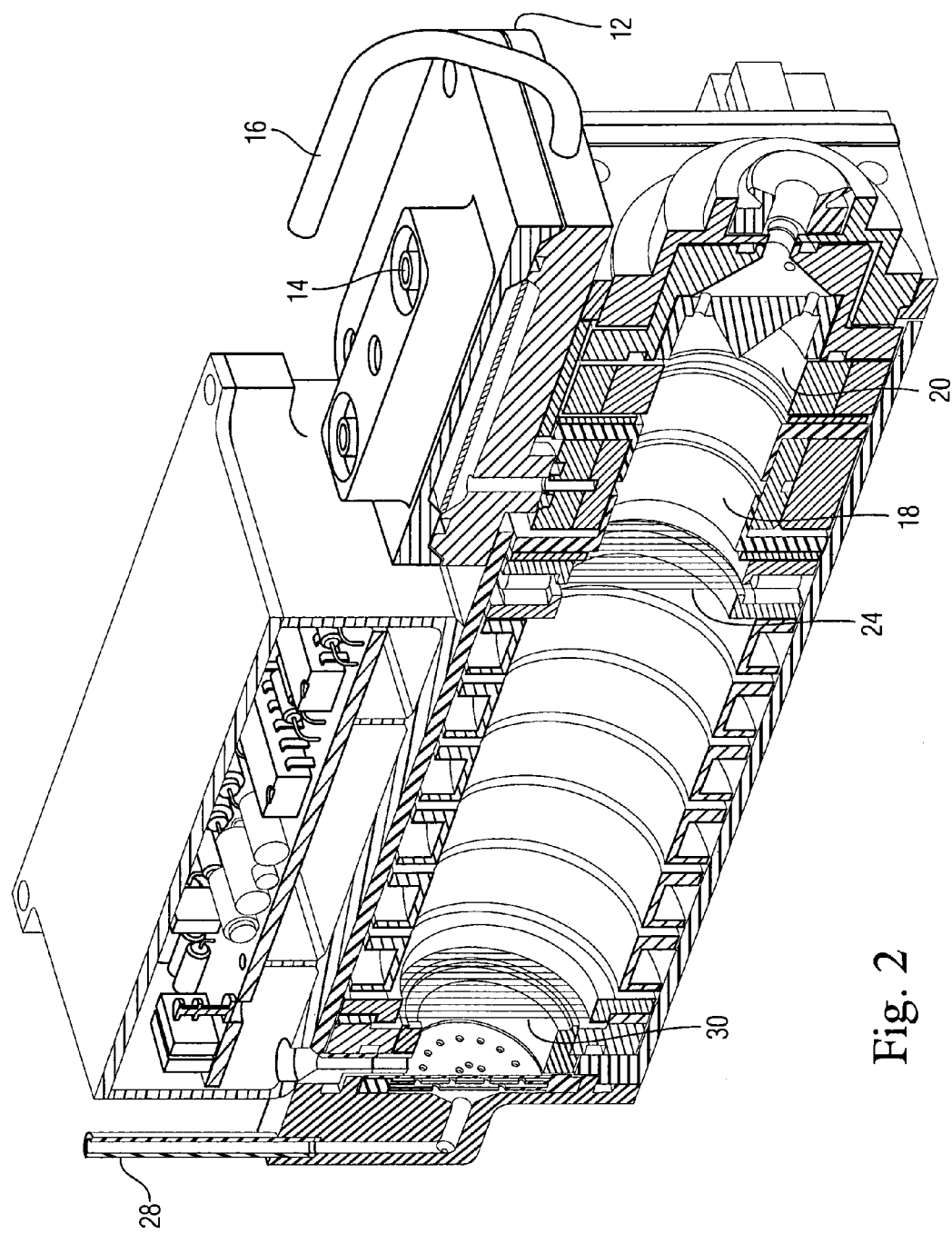
FIG. 2 is a cut-away perspective view of an ion mobility spectrometry system for use with the present invention.

The mobility spectrum is based upon the voltage induced by the plurality of sample ions passing into the drift tube during the admitting periods and striking the ion detector. Suitable embodiments and arrangements of the various components of the IMS system are known and available in the art. One embodiment is illustrated in FIG. 2.

In order to control the detector 30 and ion gate 24 and for the collection, analysis and display of the mobility spectrum information generated by the detector 30, the IMS system 10 includes one or more logic control units or processors 32 that are arranged to act as controllers, data handlers and decision makers. Suitable logic control units 32 include personal computers, including desktop and laptop computers, mainframe computers, personal digital assistants, programmable logic controllers and electrically erasable programmable read-only memory. The logic control unit 32 is in communication with the ion detector 30 and is capable of receiving data from the detector and of analyzing that data. The logic control unit 32 can be in direct contact with the ion detector 30 or can be in contact with the ion detector 30 across a wired or wireless network including local area networks, wide area networks, private area networks and secure area networks. In order to provide for the storage of data collected and generated, the logic control unit 32 is in communication with one or more databases 34. In addition to being logged in the database 34, data can be outputted on a display device 36.

The logic control unit 32 is also in communication with the ion gate 24 to control the opening and closing of the ion gate 24. In one embodiment, the logic control unit 32 is in direct communication with the ion gate 24 and controls the ion gate 24 directly. In another embodiment as illustrated in FIG. 1, the logic control unit 32 is in communication with an ion gate controller 38 that is in direct communication with the ion gate 24. In one embodiment, the ion gate controller 38 includes a transistor-transistor logic (TTL) level clock source. Although illustrated in direct communication, the logic control unit 32 and ion gate controller 38 can be arranged to operate independently from each other.

Whether the logic control unit 32, ion gate controller 38 or both are used, these systems are arranged to pulse the ion gate during pre-determined scan times using a temporally spaced pattern containing a plurality of ion admitting periods and a plurality of ion repelling periods. All of the admitting and repelling periods can be of a uniform length, or each ion admitting period can represent a distinct length of time. The length of time associated with an admitting period corresponds to a certain admission frequency.

In addition to logging the data from the ion detector 30 and controlling the ion gate 24, the logic control unit 32 is capable of processing the mobility spectrum using a combination of wavelet decomposition and statistical evaluators to produce a distinct signature associated with each sample. These distinct signatures can be stored in the database 34. In addition, a list of known agent signatures generated independently from the IMS system can be stored in the database 34, and the logic control unit 32 can be used to compare the signature of a known agent against the signature generated by an unknown sample to find a match. As used herein, the term agent includes, but is not limited to, chemicals, gases, chemicals that are considered hazardous to humans or the environment, explosives, drugs, chemical warfare agents, nerve and blister agents, microbiological constituents, biological warfare agents and petrochemicals.

Clusters of ions passing through the IMS can cause inaccurate or false readings in the IMS. Moisture or water vapor in the sample stream contributes to the production of ion clusters. Therefore, the present invention includes the apparatus 8 for removing water vapor from a gas flow in an ion mobility spectrometer. In one embodiment, the apparatus 8 includes a self-regenerating water vapor removal system capable of continuously removing water vapor from the gas flow in the IMS 10. As used herein, the gas flow includes a gas stream flowing through the IMS 10, in particular the drift tube 26, including an intake 14 gas flow, a sample, sweep or carrier gas flow 22, a counter-current gas flow 29 and combinations of these flows. As illustrated, the sample, sweep and carrier gas flows are generally the same flow, although in other embodiments these may be separate and distinct gas flows. As the water vapor is removed and accumulates in the water vapor removal apparatus 8, the water vapor removal apparatus 8 regenerates itself. Therefore, the water vapor removal apparatus 8 does not have to be removed or replaced in order to maintain or restore its ability to remove water vapor from the gas flow.

The water vapor removal system is capable of removing water vapor from any type of gas used in the gas flow including air and inert gases. Preferably, the gas flow is air. The gas flow can be introduced through the IMS in a single pass or can be a closed-loop system. Preferably, the gas flow is a closed-loop gas flow.

Figure 3:
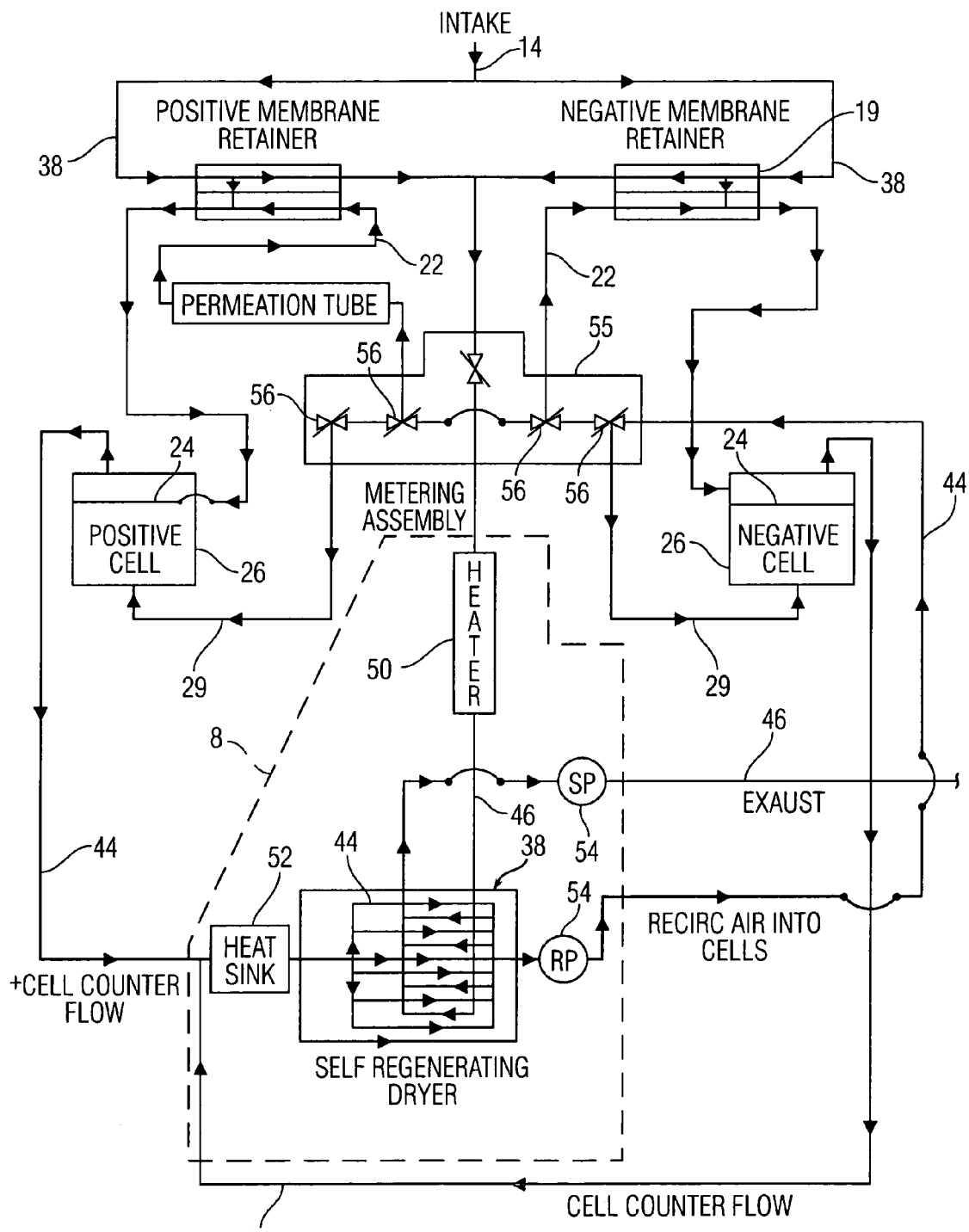
FIG. 3 is a schematic illustrating an embodiment of the gas flow through the water vapor removal apparatus and ion mobility spectrometry system in accordance with the present invention.
Figure 4:
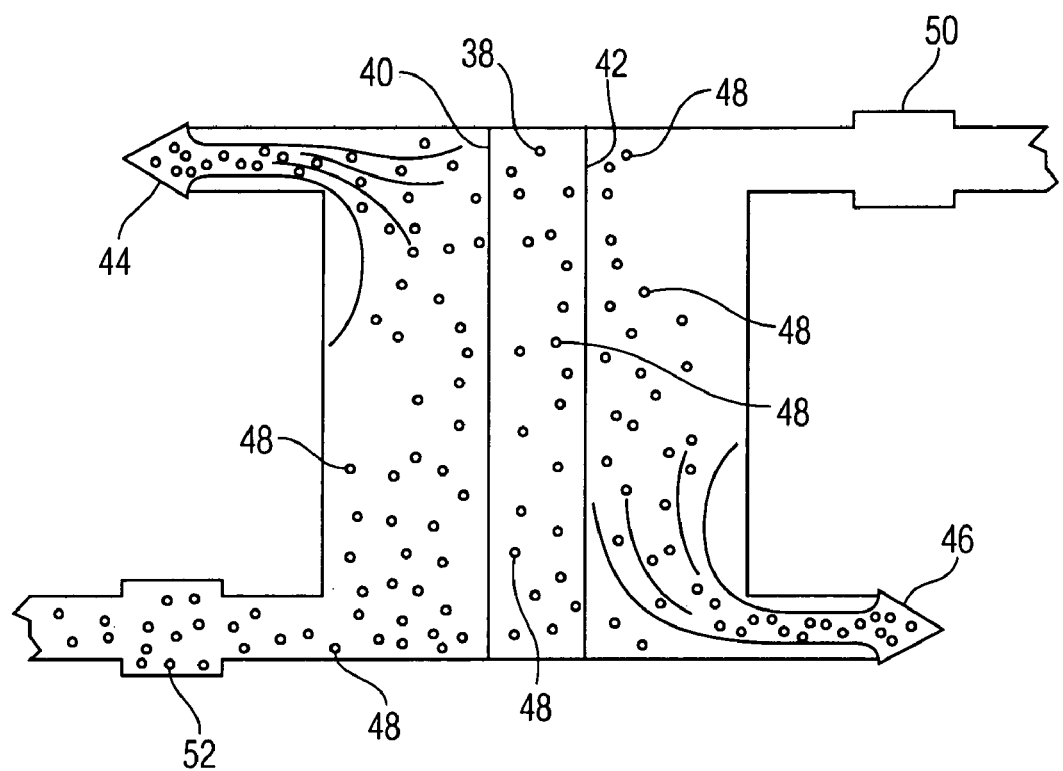
FIG. 4 is a schematic representation of a water vapor removal membrane system for use with the present invention.

Referring to FIGS. 3 and 4, the self-regenerating water vapor removal system 8 includes a water permeable membrane. Any membrane capable of selectively passing water vapor and rejecting sample ions can be used. Preferably, the membrane operates under atmospheric conditions. Suitable membranes and membrane arrangements are commercially available from the Perma Pure company of Toms River, N.J. The membrane can be arranged as a sheet or as a hollow fiber. Other suitable arrangements provide for a continuous flow of exhaust gas to be passed along one side of the membrane to remove water vapor that passes through the membrane. In addition to the membrane, the water vapor removal system 8 can include other treatment systems, for example a charcoal filter, placed in series with the water permeable membrane to remove other contaminants from the gas flow.

In one embodiment as illustrated, the water permeable membrane includes a first side 40 and a second side 42 opposite the first side 40. The gas flow 44 is disposed adjacent the first side 40, and an exhaust flow 46 for removing water vapor 48 that diffuses through the membrane disposed adjacent the second side. In one embodiment, the gas flow 44, following water vapor removal, is re-circulated as the sample or carrier flow 22 and the counter-current gas flow 29. Any exhaust gas 46 capable of sweeping or carrying the water vapor 48 from the second side 42 of the membrane 38 can be used. In one embodiment, the exhaust gas 46 is ambient air, for example taken in through the intake 14. In order to facilitate the proper selection and distribution of the gas and exhaust flows, a manifold assembly 55 having a plurality of valves 56 can be provided.

Since the solubility of water vapor in gases and air is temperature dependent, the water vapor removal apparatus 8 can alternatively include a heater 50 for heating the exhaust flow 46 prior to exposure to the second side 42 of the membrane 38 to increase the ability of the exhaust flow 46 to carry and remove the water vapor 48. Similarly, a heat sink 52 can be provided to cool the gas flow 44 before exposure to the membrane 38 to facilitate precipitation of the water vapor 48 from the gas flow 44. Suitable heaters and heat sinks are available and known in the art. Pumps 54 can also be provided to move the gas flow and exhaust flow through the system. Suitable pumps and heaters are available and known in the art. Heat sinks 52 can be arranged to be application specific.

In order to reduce the concentration of water vapor in the gas flow using a system in accordance with the present invention, the gas flow is continuously re-circulated through the self-regenerating water vapor removal system. As the gas flow is re-circulated through the system, the gas flow is passed adjacent the water-permeable membrane. In one embodiment, the gas flow is passed adjacent the first side of the membrane, and the water vapor passes through the membrane to the second side of the membrane opposite the first side. In order to remove the water vapor from the second side of the membrane, an exhaust flow is passed adjacent the second side of the membrane and exhausted from the system and the IMS. Therefore, the system and the membrane are regenerated in-situ without being removed or replaced and can continue to remove water vapor from the re-circulated gas flow. In one embodiment, the gas flow is continuously re-circulated through the ion mobility spectrometer and the water vapor removal system in a closed-loop.

In one embodiment in order to increase the ability of the exhaust gas to remove water vapor, the exhaust flow is heated prior to passing the exhaust flow adjacent the second side of the membrane. In another embodiment, in order to enhance removal of the water from the gas flow, the gas flow is cooled prior to passing the gas flow adjacent the first side of the membrane. Additional treatment for the flow gas can be provided by passing the gas flow through a charcoal filter.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments, which would come within the spirit and scope of the present invention.

What is claimed is:

1. A material analysis apparatus, comprising:
an ion mobility spectrometer; and
a self-regenerating water vapor removal system, comprising:
   at least one water permeable membrane;
   a first and second gas port, said first and second gas ports positioned on a first side of said at least one water permeable membrane; and
   a third gas port positioned on a second side of said at least one water permeable membrane; and
   a heater portion is coupled between said second gas port and said input portion of said ion mobility spectrometer
wherein said first gas port is coupled to a gas sample input portion, said second gas port is coupled to an input portion of said ion mobility spectrometer and said third port being adapted to receive an exhaust gas comprising water vapor removed from gas received from said first gas port.

2. A material analysis apparatus as in claim 1, wherein the self-regenerating water vapor removal system further comprises a second water penneable membrane and a manifold portion coupled between said input portion of said ion mobility spectrometer and said second gas port.

3. A material analysis apparatus as in claim 1, wherein the self-regenerating water vapor removal system further comprises a dryer.

4. A material analysis apparatus as in claim 1, wherein the self-regenerating water vapor removal system further comprises a condenser.

5. A material analysis apparatus as in claim 1, wherein a heat sink is coupled between said second gas port and said input portion of said ion mobility spectrometer.

6. A method of manufacturing a material analysis apparatus, comprising:

providing an ion mobility spectrometer;
coupling a self-regenerating water vapor removal system to said ion mobility spectrometer, said self-regenerating water vapor removal system comprising:
at least one water permeable membrane;
a first and second gas port, said first and second gas ports positioned on a first side of said at least one water permeable membrane;
a third gas port positioned on a second side of said at least one water permeable membrane;
providing a heater portion coupled between said second gas port and said input portion of said ion mobility spectrometer;
wherein said first gas port is adapted to receive a gas sample from a gas sample input portion, said second gas port is coupled to an input portion of said ion mobility spectrometer and said third port being adapted to receive an exhaust gas comprising water vapor removed from said gas sample.

7. A method of manufacturing a material analysis apparatus as in claim 6, further comprising providing a dryer.

8. A method of manufacturing a material analysis apparatus as in claim 6, further comprising providing a condenser coupled between said second gas port and said input portion of said ion mobility spectrometer.

9. A method of manufacturing a material analysis apparatus as in claim 6, further comprising providing a heat sink adapted to cool said gas sample prior to said gas sample being moved to be in contact with said membrane.

10. A method of manufacturing a material analysis apparatus as in claim 6, further comprising:
providing a heater adapted for heating the exhaust flow to increase removal of water vapor from the second side of the membrane; and
providing a heat sink adapted to cool said gas sample prior to said gas sample being moved to be in contact with said membrane.

* * * * *